United States Patent [19]
Kishimoto

[11] Patent Number: 5,223,611
[45] Date of Patent: Jun. 29, 1993

[54] DNA ENCODING FOR HUMAN GP130 PROTEIN

[76] Inventor: Tadamitsu Kishimoto, 5-31, Nakano-cho 3-chome, Tondabayashi-shi, Osaka, Japan

[21] Appl. No.: 889,131

[22] Filed: May 27, 1992

Related U.S. Application Data

[63] Continuation of Ser. No. 561,564, Aug. 2, 1990, Pat. No. 5,132,403.

[30] Foreign Application Priority Data

Aug. 3, 1989 [JP] Japan .................. 1-200230
May 31, 1990 [JP] Japan .................. 2-140069

[51] Int. Cl.$^5$ .......................................... C07H 21/00
[52] U.S. Cl. ................... 530/351; 435/69.1; 435/320.1; 536/23.5
[58] Field of Search .......... 536/27; 435/69.1, 320.1; 530/351

[56] References Cited

PUBLICATIONS

Schwabe et al. *Lympokine Res.* 9(4):550 (1990).
Schwabe et al. *Progess in Leukocyte Biol.* 10A (1989).
Kishimoto, "The Biology of Interleukin-6," *Blood,* 74:1-10, (1989).
Kishimoto, "Molecular Regulation of B Lymphocyte Resonse," *Ann. Rev. Immunol.,* 6:485-512, (1988).
Hibi et al., "Characterization and Molecular Cloning of Interleukin-6 Receptor (IL-6R)-Associated Signal Transducer," *Faseb,* (Feb. Am. Soc. Exp. Biol.), 4(7):A1918, Abstract No. 1311, (Apr. 26, 1990).
Taga et al., "Interleukin-6 Triggers The Association of its Receptor With A Possible Signal Transducer, gp130," *Cell,* 56(3):573-581, (1989).
Short et al., "A Zap a Bacteriophage δ Expression Vector With In Vivo Excision Properties," *Nucleic Acids Research,* 16(15):7583-7600, (1988).
Cold Spring Harbor Syposia On Quantitative Biology, 54(2):713-722, (CSH Laboratory Press, 1989).
Young et al., "Efficient Isolation of Genes by Using Antibody Probes," *Proc. Natl. Acad. Sci USA,* 80:1194-1198, (1983).

*Primary Examiner*—Robert J. Hill, Jr.
*Assistant Examiner*—Shelly J. Guest
*Attorney, Agent, or Firm*—Foley & Lardner

[57] ABSTRACT

Human gp130 protein having at least the following properties: (1) the protein has an affinity with a complex of IL-6 (interleukin-6) and an IL-6 receptor (interleukin-6 receptor); (2) the protein shows an apparent molecular weight of 130 kDa in SDS-polyacrylamide electrophoresis; and (3) the protein participates in the transmission of IL-6 signal; DNA coding for the protein, an expression plamid containing the DNA; and a process for production of the protein using the expression plasmid.

5 Claims, 10 Drawing Sheets

Fig. 7-1

```
GAATTCGGGG CCGGGGCGAG CAGCCAAAAG GCCCGCGGAG TCGCGCTGGG      50

CCGCCCCGGC GCAGCTGAAC CGGGGGCCGC GCCTGCCAGG CCGACGGGTC     100

TGGCCCAGCC TGGCGCCAAG GGGTTCGTGC GCTGTGGAGA CGCGGAGGGT     150

CGAGGCGGCG CGGCCTGAGT GAAACCCAAT GGAAAAAGCA TGACATTTAG     200

AAGTAGAAGA CTTAGCTTCA AATCCCTACT CCTTCACTTA CTAATTTTGT     250

5
                 Met Leu Thr Leu Gln Thr Trp
GATTTGGAAA TATCCGCGCA AG ATG TTG ACG TTG CAG ACT TGG       293

10                 15                 20
Val Val Gln Ala Leu Phe Ile Phe Leu Thr Thr Glu Ser Thr
GTA GTG CAA GCC TTG TTT ATT TTC CTC ACC ACT GAA TCT ACA    335

25                 30                 35
Gly Glu Leu Leu Asp Pro Cys Gly Tyr Ile Ser Pro Glu Ser
GGT GAA CTT CTA GAT CCA TGT GGT TAT ATC AGT CCT GAA TCT    377

40                 45
Pro Val Val Gln Leu His Ser Asn Phe Thr Ala Val Cys Val
CCA GTT GTA CAA CTT CAT TCT AAT TTC ACT GCA GTT TGT GTG    419

50                 55                 60
Leu Lys Glu Lys Cys Met Asp Tyr Phe His Val Asn Ala Asn
CTA AAG GAA AAA TGT ATG GAT TAT TTT CAT GTA AAT GCT AAT    461

65                 70                 75
Tyr Ile Val Trp Lys Thr Asn His Phe Thr Ile Pro Lys Glu
TAC ATT GTC TGG AAA ACA AAC CAT TTT ACT ATT CCT AAG GAG    503

80                 85                 90
Gln Tyr Thr Ile Ile Asn Arg Thr Ala Ser Ser Val Thr Phe
CAA TAT ACT ATC ATA AAC AGA ACA GCA TCC AGT GTC ACC TTT    545

95                 100                105
Thr Asp Ile Ala Ser Leu Asn Ile Gln Leu Thr Cys Asn Ile
ACA GAT ATA GCT TCA TTA AAT ATT CAG CTC ACT TGC AAC ATT    587

110                 115
Leu Thr Phe Gly Gln Leu Glu Gln Asn Val Tyr Gly Ile Thr
CTT ACA TTC GGA CAG CTT GAA CAG AAT GTT TAT GGA ATC ACA    629

120                 125                 130
Ile Ile Ser Gly Leu Pro Pro Glu Lys Pro Lys Asn Leu Ser
ATA ATT TCA GGC TTG CCT CCA GAA AAA CCT AAA AAT TTG AGT    671
```

Fig. 7-2

```
             135                       140                        145
    Cys Ile Val Asn Glu Gly Lys Lys Met Arg Cys Glu Trp Asp
    TGC ATT GTG AAC GAG GGG AAG AAA ATG AGG TGT GAG TGG GAT              713

150                       155                        160
    Gly Gly Arg Glu Thr His Leu Glu Thr Asn Phe Thr Leu Lys
    GGT GGA AGG GAA ACA CAC TTG GAG ACA AAC TTC ACT TTA AAA              755

165                       170                        175
    Ser Glu Trp Ala Thr His Lys Phe Ala Asp Cys Lys Ala Lys
    TCT GAA TGG GCA ACA CAC AAG TTT GCT GAT TGC AAA GCA AAA              797

180                       185
    Arg Asp Thr Pro Thr Ser Cys Thr Val Asp Tyr Ser Thr Val
    CGT GAC ACC CCC ACC TCA TGC ACT GTT GAT TAT TCT ACT GTG              839

190                       195                       200
    Tyr Phe Val Asn Ile Glu Val Trp Val Glu Ala Glu Asn Ala
    TAT TTT GTC AAC ATT GAA GTC TGG GTA GAA GCA GAG AAT GCC              881

205                       210                       215
    Leu Gly Lys Val Thr Ser Asp His Ile Asn Phe Asp Pro Val
    CTT GGG AAG GTT ACA TCA GAT CAT ATC AAT TTT GAT CCT GTA              923

220                       225                       230
    Tyr Lys Val Lys Pro Asn Pro Pro His Asn Leu Ser Val Ile
    TAT AAA GTG AAG CCC AAT CCG CCA CAT AAT TTA TCA GTG ATC              965

235                       240                       245
    Asn Ser Glu Glu Leu Ser Ser Ile Leu Lys Leu Thr Trp Thr
    AAC TCA GAG GAA CTG TCT AGT ATC TTA AAA TTG ACA TGG ACC             1007

250                       255
    Asn Pro Ser Ile Lys Ser Val Ile Ile Leu Lys Tyr Asn Ile             1049
    AAC CCA AGT ATT AAG AGT GTT ATA ATA CTA AAA TAT AAC ATT 260                       265                       270
    Gln Tyr Arg Thr Lys Asp Ala Ser Thr Trp Ser Gln Ile Pro
    CAA TAT AGG ACC AAA GAT GCC TCA ACT TGG AGC CAG ATT CCT             1091

275                       280                       285
    Pro Glu Asp Thr Ala Ser Thr Arg Ser Ser Phe Thr Val Gln
    CCT GAA GAC ACA GCA TCC ACC CGA TCT TCA TTC ACT GTC CAA             1133

290                       295                       300
    Asp Leu Lys Pro Phe Thr Glu Tyr Val Phe Arg Ile Arg Cys
    GAC CTT AAA CCT TTT ACA GAA TAT GTG TTT AGG ATT CGC TGT             1175
```

Fig. 7-3

```
                    305                           310                           315
Met Lys Glu Asp Gly Lys Gly Tyr Trp Ser Asp Trp Ser Glu
ATG AAG GAA GAT GGT AAG GGA TAC TGG AGT GAC TGG AGT GAA          1217

320                           325
Glu Ala Ser Gly Ile Thr Tyr Glu Asp Arg Pro Ser Lys Ala
GAA GCA AGT GGG ATC ACC TAT GAA GAT AGA CCA TCT AAA GCA          1259

330                           335                           340
Pro Ser Phe Trp Tyr Lys Ile Asp Pro Ser His Thr Gln Gly
CCA AGT TTC TGG TAT AAA ATA GAT CCA TCC CAT ACT CAA GGC          1301

345                           350                           355
Tyr Arg Thr Val Gln Leu Val Trp Lys Thr Leu Pro Pro Phe
TAC AGA ACT GTA CAA CTC GTG TGG AAG ACA TTG CCT CCT TTT          1343

360                           365                           370
Glu Ala Asn Gly Lys Ile Leu Asp Tyr Glu Val Thr Leu Thr
GAA GCC AAT GGA AAA ATC TTG GAT TAT GAA GTG ACT CTC ACA          1385

375                           380                           385
Arg Trp Lys Ser His Leu Gln Asn Tyr Thr Val Asn Ala Thr
AGA TGG AAA TCA CAT TTA CAA AAT TAC ACA GTT AAT GCC ACA          1427

390                           395
Lys Leu Thr Val Asn Leu Thr Asn Asp Arg Tyr Leu Ala Thr
AAA CTG ACA GTA AAT CTC ACA AAT GAT CGC TAT CTA GCA ACC          1469

400                           405                           410
Leu Thr Val Arg Asn Leu Val Gly Lys Ser Asp Ala Ala Val
CTA ACA GTA AGA AAT CTT GTT GGC AAA TCA GAT GCA GCT GTT          1511

415                           420                           425
Leu Thr Ile Pro Ala Cys Asp Phe Gln Ala Thr His Pro Val
TTA ACT ATC CCT GCC TGT GAC TTT CAA GCT ACT CAC CCT GTA          1553

430                           435                           440
Met Asp Leu Lys Ala Phe Pro Lys Asp Asn Met Leu Trp Val
ATG GAT CTT AAA GCA TTC CCC AAA GAT AAC ATG CTT TGG GTG          1595

445                           450                           455
Glu Trp Thr Thr Pro Arg Glu Ser Val Lys Lys Tyr Ile Leu
GAA TGG ACT ACT CCA AGG GAA TCT GTA AAG AAA TAT ATA CTT          1637

460                           465
Glu Trp Cys Val Leu Ser Asp Lys Ala Pro Cys Ile Thr Asp
GAG TGG TGT GTG TTA TCA GAT AAA GCA CCC TGT ATC ACA GAC          1679
```

Fig. 7-4

```
        470                      475                      480
Trp Gln Gln Glu Asp Gly Thr Val His Arg Thr Tyr Leu Arg
TGG CAA CAA GAA GAT GGT ACC GTG CAT CGC ACC TAT TTA AGA      1721

485                      490                      495
Gly Asn Leu Ala Glu Ser Lys Cys Tyr Leu Ile Thr Val Thr
GGG AAC TTA GCA GAG AGC AAA TGC TAT TTG ATA ACA GTT ACT      1763

500                      505                      510
Pro Val Tyr Ala Asp Gly Pro Gly Ser Pro Glu Ser Ile Lys
CCA GTA TAT GCT GAT GGA CCA GGA AGC CCT GAA TCC ATA AAG      1805

515                      520                      525
Ala Tyr Leu Lys Gln Ala Pro Pro Ser Lys Gly Pro Thr Val
GCA TAC CTT AAA CAA GCT CCA CCT TCC AAA GGA CCT ACT GTT      1847

530                      535
Arg Thr Lys Lys Val Gly Lys Asn Glu Ala Val Leu Glu Trp
CGG ACA AAA AAA GTA GGG AAA AAC GAA GCT GTC TTA GAG TGG      1889

540                      545                      550
Asp Gln Leu Pro Val Asp Val Gln Asn Gly Phe Ile Arg Asn
GAC CAA CTT CCT GTT GAT GTT CAG AAT GGA TTT ATC AGA AAT      1931

555                      560                      565
Tyr Thr Ile Phe Tyr Arg Thr Ile Ile Gly Asn Glu Thr Ala
TAT ACT ATA TTT TAT AGA ACC ATC ATT GGA AAT GAA ACT GCT      1973

570                      575                      580
Val Asn Val Asp Ser Ser His Thr Glu Tyr Thr Leu Ser Ser
GTG AAT GTG GAT TCT TCC CAC ACA GAA TAT ACA TTG TCC TCT      2015

585                      590                      595
Leu Thr Ser Asp Thr Leu Tyr Met Val Arg Met Ala Ala Tyr
TTG ACT AGT GAC ACA TTG TAC ATG GTA CGA ATG GCA GCA TAC      2057

600                      605
Thr Asp Glu Gly Gly Lys Asp Gly Pro Glu Phe Thr Phe Thr
ACA GAT GAA GGT GGG AAG GAT GGT CCA GAA TTC ACT TTT ACT      2099

610                      615                      620
Thr Pro Lys Phe Ala Gln Gly Glu Ile Glu Ala Ile Val Val
ACC CCA AAG TTT GCT CAA GGA GAA ATT GAA GCC ATA GTC GTG      2141

625                      630                      635
Pro Val Cys Leu Ala Phe Leu Leu Thr Thr Leu Leu Gly Val
CCT GTT TGC TTA GCA TTC CTA TTG ACA ACT CTT CTG GGA GTG      2183

640                      645                      650
Leu Phe Cys Phe Asn Lys Arg Asp Leu Ile Lys Lys His Ile
CTG TTC TGC TTT AAT AAG CGA GAC CTA ATT AAA AAA CAC ATC      2225
```

Fig.7-5

```
             655                      660                      665
Trp Pro Asn Val Pro Asp Pro Ser Lys Ser His Ile Ala Gln
TGG CCT AAT GTT CCA GAT CCT TCA AAG AGT CAT ATT GCC CAG          2267

670                      675
Trp Ser Pro His Thr Pro Pro Arg His Asn Phe Asn Ser Lys
TGG TCA CCT CAC ACT CCT CCA AGG CAC AAT TTT AAT TCA AAA          2309

680                      685                      690
Asp Gln Met Tyr Ser Asp Gly Asn Phe Thr Asp Val Ser Val
GAT CAA ATG TAT TCA GAT GGC AAT TTC ACT GAT GTA AGT GTT          2351

695                      700                      705
Val Glu Ile Glu Ala Asn Asp Lys Lys Pro Phe Pro Glu Asp
GTG GAA ATA GAA GCA AAT GAC AAA AAG CCT TTT CCA GAA GAT          2393

710                      715                      720
Leu Lys Ser Leu Asp Leu Phe Lys Lys Glu Lys Ile Asn Thr
CTG AAA TCA TTG GAC CTG TTC AAA AAG GAA AAA ATT AAT ACT          2435

725                      730                      735
Glu Gly His Ser Ser Gly Ile Gly Gly Ser Ser Cys Met Ser
GAA GGA CAC AGC AGT GGT ATT GGG GGG TCT TCA TGC ATG TCA          2477

740                      745
Ser Ser Arg Pro Ser Ile Ser Ser Ser Asp Glu Asn Glu Ser
TCT TCT AGG CCA AGC ATT TCT AGC AGT GAT GAA AAT GAA TCT          2519

750                      755                      760
Ser Gln Asn Thr Ser Ser Thr Val Gln Tyr Ser Thr Val Val
TCA CAA AAC ACT TCG AGC ACT GTC CAG TAT TCT ACC GTG GTA          2561

765                      770                      775
His Ser Gly Tyr Arg His Gln Val Pro Ser Val Gln Val Phe
CAC AGT GGC TAC AGA CAC CAA GTT CCG TCA GTC CAA GTC TTC          2603

780                      785                      790
Ser Arg Ser Glu Ser Thr Gln Pro Leu Leu Asp Ser Glu Glu
TCA AGA TCC GAG TCT ACC CAG CCC TTG TTA GAT TCA GAG GAG          2645

795                      800                      805
Arg Pro Glu Asp Leu Gln Leu Val Asp His Val Asp Gly Gly
CGG CCA GAA GAT CTA CAA TTA GTA GAT CAT GTA GAT GGC GGT          2687
```

Fig. 7-6

```
                    810                      815
Asp Gly Ile Leu Pro Arg Gln Gln Tyr Phe Lys Gln Asn Cys
GAT GGT ATT TTG CCC AGG CAA CAG TAC TTC AAA CAG AAC TGC         2729

820                 825                 830
Ser Gln His Glu Ser Ser Pro Asp Ile Ser His Phe Glu Arg
AGT CAG CAT GAA TCC AGT CCA GAT ATT TCA CAT TTT GAA AGG         2771

835                 840                 845
Ser Lys Gln Val Ser Ser Val Asn Glu Glu Asp Phe Val Arg
TCA AAG CAA GTT TCA TCA GTC AAT GAG GAA GAT TTT GTT AGA         2813

850                 855                 860
Leu Lys Gln Gln Ile Ser Asp His Ile Ser Gln Ser Cys Gly
CTT AAA CAG CAG ATT TCA GAT CAT ATT TCA CAA TCC TGT GGA         2855

865                 870                 875
Ser Gly Gln Met Lys Met Phe Gln Glu Val Ser Ala Ala Asp
TCT GGG CAA ATG AAA ATG TTT CAG GAA GTT TCT GCA GCA GAT         2897

880                 885
Ala Phe Gly Pro Gly Thr Glu Gly Gln Val Glu Arg Phe Glu
GCT TTT GGT CCA GGT ACT GAG GGA CAA GTA GAA AGA TTT GAA         2939

890                 895                 900
Thr Val Gly Met Glu Ala Ala Thr Asp Glu Gly Met Pro Lys
ACA GTT GGC ATG GAG GCT GCG ACT GAT GAA GGC ATG CCT AAA         2981

905                 910                 915
Ser Tyr Leu Pro Gln Thr Val Arg Gln Gly Gly Tyr Met Pro
AGT TAC TTA CCA CAG ACT GTA CGG CAA GGC GGC TAC ATG CCT         3023

918
Gln
CAG TGAAGGACTA GTAGTTCCTG CTACAACTTC AGCAGTACCT                 3066

ATAAAGTAAA GCTAAAATGA TTTTATCTGT GAATTC                         3102
```

DNA ENCODING FOR HUMAN GP130 PROTEIN

This application is a division of application Ser. No. 07/561,564, filed Aug. 2, 1990, now U.S. Pat. No. 5,132,403.

BACKGROUND OF THE INVENTION (1) Field of the Invention

The present invention relates to a human gp130 protein, which is a protein participating in the transmission of an IL-6 signal, a DNA coding for this protein, and a means for and a method of producing this protein by genetic engineering.

(2) Description of the Related Art

Interleukin-6 (IL-6) is a protein participating broadly in the proliferation and differentiation of an organism, and is characterized in that the protein plays an important role in defense system of an organism such as immunity, hematopoiesis or inflammation (see Kishimoto, Blood, 74, page 1, 1989). It is reported that an abnormal production of IL-6 may become a factor in the cause of various autoimmune diseases (see Kishimoto and Hirano, Ann. Rev. Immunol., 6 page 485, 1988).

The inventors isolated a gene for human IL-6 receptor on the cell membrane, which is specifically bonded to human IL-6, and determined the primary structure thereof (see Japanese Patent Application No. 63-194885). Then the inventors isolated a gene of mouse IL-6 receptor on the cell membrane, which is specifically bonded to mouse IL-6, and determined the primary structure thereof (see Japanese Patent Application No. 1-292230). Furthermore, the inventors prepared a soluble IL-6 receptor (extracellular portion of an IL-6 receptor), considered to be usable for a therapeutic or diagnostic medicine, from the human IL-6 receptor gene as the starting material (see Japanese Patent Application No. 1-9774).

SUMMARY OF THE INVENTION

An artificial control of the function of IL-6 strongly exerting physiological activities in a organism is considered usable as a new mechanism for the therapy of various diseases, and knowledge of the course of the transmission of an IL-6 signal is important in the development of a medicinal substance for enhancing or inhibiting the function of IL-6.

The inventors investigated the mechanism of the transmission of IL-6 signal, and as a result, found that, in addition to the IL-6 and IL-6 receptor, there exists, as a third factor, a protein participating in the transmission of IL-6 signal. Since this protein has an apparent molecular weight of 130 kb, the inventors named this protein "human gp130". To further analyze the transmission of IL-6 signal or to develop a soluble gp130 (the extracellular portion of a gp130 protein) as an inhibitor for IL-6, a large quantity of a purified product of soluble gp130 must be obtained but the amount of gp130 produced in an organism is very small A DNA sequence coding for pg130 is indispensable for producing gp130 in a large quantity by a genetic engineering method.

Therefore, a primary object of the present invention is to provide a human gp130, a DNA coding for the gp130, and a process for producing the gp130 by using the DNA.

The inventors carried out research into the transmission of IL-6 signal, and found a protein on the cell membrane which participates in the transmission of IL-6 signal, and furthermore, proved that the IL-6 receptor on the cell membrane is bonded to this membrane protein through the bonding to IL-6, this membrane protein bears the transmission of IL-6 signal, and the intracellular region of the IL-6 receptor does not participate in the transmission of IL-6 signal.

Also, the inventors succeeded in cloning a DNA coding for human gp130, and determined the nucleotide sequence of this DNA.

The present invention is based on the results of these researches. More specifically, the present invention provides a gp130 participating in the transmission of IL-6 signal; a DNA sequence coding human gp130; a replicable vector capable of expressing this DNA sequence in a recombination microorganism or cultured cell; a microorganism or cultured cell transformed by this expression vector; and a process for the production of human gp130, which comprises expressing a DNA sequence coding gp130 in this microorganism or cultured cell.

BRIEF DESCRIPTION OF THE DRAWINGS

FIGS. 7-1 through 7-6 show the results of the analysis of the nucleotide sequence of insert DNA of pGP130, i.e., DNA coding for human gp130, and show the presumed amino acid sequence of a protein, i.e., human gp130 produced when this DNA sequence is expressed, in which the underlined portion represents a hydrophobic amino acid region on the N-terminal side and the double-underlined portion represents a hydrophobic amino acid region on the C-terminal side; and, FIG. 8 shows the results of a Northern blot analysis of various cells conducted by using human gp130 cDNA as the probe.

DESCRIPTION OF THE PREFERRED EMBODIMENTS

1. gp130 Protein

Figure 1:
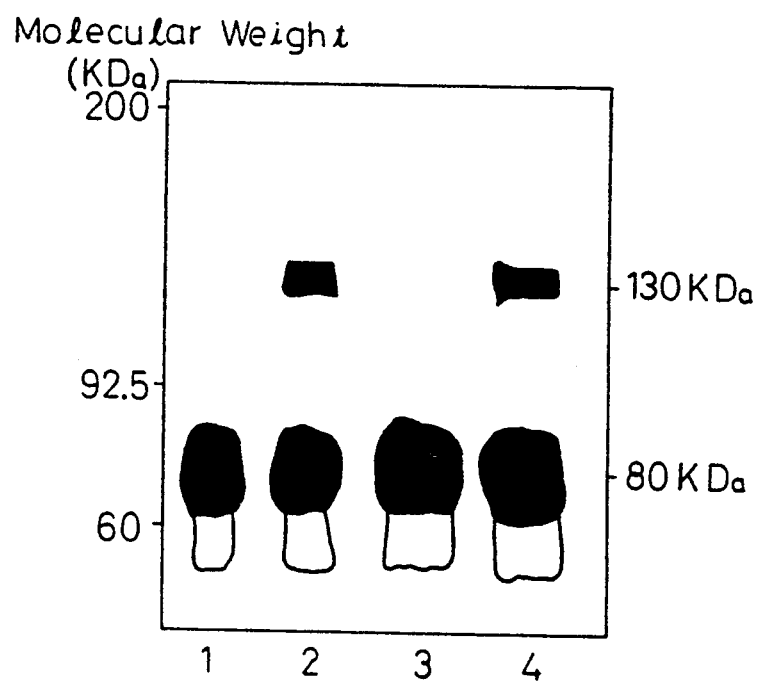
FIG. 1 shows autoradiographic patterns obtained when U266 cells internally labelled with $^{35}$S-methionine are lysed after treatment with IL-6 (lanes 2 and 4) or without treatment with IL-6 (lanes 1 and 3), and then immunoprecipitated by an IL-6 receptor antibody MT18 immobilized on Sepharose B4, and SDS/PAGE is carried out under non-reducing conditions (lanes 1 and 2) or under reducing conditions (lanes 3 and 4)

The cell membrane-derived protein participating in the transmission of IL-6 signal according to the present invention, i.e., gp130, exerts an important function when IL-6 is bonded to an IL-6 receptor to finally cause various cells to exert biological activities such as proliferation and differentiation, and in the natural state, this protein is located on the cell membrane. The IL-6 referred to herein includes IL-6 produced in an organism, IL-6 produced by a genetic engineering method, and derivatives thereof. Furthermore, the IL-6 receptor includes a IL-6 receptor present on the cell membrane produced in an organism or by a genetic engineering method, a soluble IL-6 receptor isolated from the cell membrane, and derivatives thereof.

This protein has the following properties.

(1) The protein is bonded to a complex of IL-6 and an IL-6 receptor.

(2) The protein is not bonded to IL-6 alone or IL-6 receptor alone.

(3) The protein shows an apparent molecular weight of 130 kDa in the SDS-polyacrylamide gel electrophoresis. This protein participates in the transmission of IL-6 signal and in the natural state, has an amino acid sequence (referred to herein as formula (I)) of from Met at 1-site to Gln at 918-site in FIG. 7. In the present invention, the protein may be any protein having the above-mentioned amino acid sequence, and a protein or polypeptide having a portion of the above-mentioned amino acid sequence that makes a contribution to the specific bonding to a complex of IL-6 and IL-6 receptor. Namely, all proteins and polypeptides having an amino acid sequence in which at least one amino acid residue of the above-mentioned amino acid sequence is substituted by another amino acid residue(s), or at least on amino acid residue is deleted from the above-mentioned amino acid sequence, or at least one amino acid is added to the above-mentioned amino acid sequence, and still retaining a capacity of being specifically bonded to complex of IL-6 and IL-6 receptor, are included within the scope of the pg130 of the present invention. For example, there can be mentioned proteins in which an amino acid sequence or amino acid residue not making a contribution to the bonding to the complex of IL-6 and IL-6 receptor in the above-mentioned amino acid sequence is modified by substitution, deficiency or insertion, proteins in which an amino acid sequence and/or an amino acid residue portion is added to the N-terminal side and/or the C-terminal side of the above-mentioned amino acid sequence, and proteins formed by a fusion of another protein, such as a human growth hormone, to the above-mentioned amino acid sequence.

The amino acid sequence represented by formula (I) consists of 918 amino acid residues, and hydrophobic amino residues are located in the region of from leucine at the second position from the N-terminal side to glycine located at the 22nd position and the region of from alanine at the 620th position to phenylalanine at the 641st position. It is considered that, of these two regions, the former region is a signal peptide region and the latter region is a membrane penetration region.

2. DNA Sequence

DNA coding for human gp130 protein of the present invention encodes, for example, an amino acid sequence of from Met at 1-position to Gln at 918-position in FIG. 7. Representative cDNA has a base sequence of from A at 273-position to G at 3026-position in FIG. 7. The DNA sequence of the present invention includes not only the above-mentioned DNA sequence but also DNA in which at least one nucleotide of the above-mentioned DNA sequence is substituted with another nucleotide, or at least one nucleotide is deleted from the above-mentioned DNA sequence, or at least one nucleotide is added to the above-mentioned DNA sequence, and which codes for a protein having a capacity of being specifically bonded to the IL-6/IL-6 receptor complex. For example, there can be mentioned DNA sequences coding proteins having the amino acid sequences as mentioned in (1) above.

3. Process for Preparation of gp130 Protein

According to the first process of the present invention, the cell membrane-derived protein participating in the transmission of IL-6 signal is prepared from animal cells producing this protein. As the cells, there can be mentioned IL-6 receptor-producing cells, for example, human myeloma cell U266, mouse leukemia cell line M1, and human B cell line CL4. The protein of the present invention participating in the transmission of IL-6 signal also can be produced by cells not producing IL-6 receptor. As the cells of this type, mouse B cell line M12, human T cell line Jurkat, and mouse T cell line CTLL2 can be mentioned. Namely, the protein participating in the transmission of IL-6 signal according to the present invention can be obtained from these cells.

As pointed out hereinbefore, the protein of the present invention is bonded to the IL-6 receptor in the presence of IL-6 but is not bonded to the IL-6 receptor in the absence of IL-6, and therefore, the protein of the present invention can be isolated by utilizing this property.

For example, to isolate the protein from cells producing both the IL-6 receptor and the protein of the present invention, a process can be adopted in which the producing cells are cultured, IL-6 is artificially added to the cultured cells, incubation is carried out for a time sufficient to allow a reaction between the cells and the added IL-6 under physiological conditions, for example, for about 30 minutes at about 37° C. in a conventional culture medium such as RPMI1640, and the cells are then lysed by a customary method, for example, by a treatment with a triethanolamine buffer solution containing 1% of digitonine, whereby a cell lysate containing a complex in which IL-6, the IL-6 receptor and the protein of the present invention are bonded together is obtained. Alternatively, after the cells are lysed by a customary method, incubation is carried out in the above-mentioned manner to obtain a cell lysate containing the above-mentioned complex. An antibody to IL-6 receptor, for example, MT18 antibody (prepared according to Referential Example 1 given hereinafter; see Japanese Patent Application No. 63-194885) is immobilized by a solid carrier, for example, Sepharose 4B, by the cyanogen bromide activation method. By placing this immobilized antibody to IL-6 receptor in contact with the above-mentioned cell lysate, the complex containing the protein of the present invention is immobilized on the above-mentioned solid carrier through the specific reaction between the IL-6 receptor and the IL-6 receptor antibody. Then, this solid carrier is washed to remove non-specifically bonded or adhering impurities, and the complex is eluted from the solid carrier by a conventional means using, for example, urea or guanidine, to free the desired protein of the present invention from the IL-6 receptor-containing protein complex.

To isolate and purify the desired protein of the present invention from the obtained solution, customary means adopted for the isolation and purification of proteins, such as precipitation using ammonium sulfate, column chromatography, for example, reversed phase chromatography and ion exchange chromatography, and electrophoresis can be used. During this isolation and purification process, an active fraction can be selected by utilizing the bonding to the IL-6 receptor in the presence of IL-6, non-bonding to the IL-6 receptor in the absence of IL-6, and confirming the molecular weight of 130 kDa as the criterion.

Where cells producing the protein of the present invention but not producing the IL-6 receptor are used, incubation is carried out in the presence of a soluble IL-6 receptor and IL-6, and the cells are then lysed to obtain a cell lysate containing an IL-6/IL-6 receptor/-desired protein complex. Alternatively, the above-mentioned cells producing the protein of the present invention are lysed, an incubation of IL-6 and the IL-6 receptor is carried out, and finally, a cell lysate containing an IL-6/IL-6 receptor/desired protein complex is obtained. The desired protein can be isolated and purified from this cell lysate in the above-mentioned manner.

The second process for the production of the protein participating in the transmission of IL-6 signal according to the present invention utilizes gene recombination. In this process, DNA coding for an amino acid sequence of a protein on the cell membrane, which participates in the transmission of IL-6 signal, can be obtained by various methods. For example, cDNA library is formed from cells expressing the above-mentioned protein thereon, such as human myeloma cells, according to customary procedures, and this library is selected according to various methods, for example, the method in which a probe designed on the basis of a partial amino acid sequence of the purified protein is used, and the method in which cDNA is expressed and the selection is made based on the property of the produced protein, for example, the specific bonding to the IL-6-bonded IL-6 receptor. The protein of the present invention is produced by expressing the thus-cloned DNA according to customary procedures.

4. DNA Coding gp130 Protein

The DNA to be used for the above-mentioned process can be prepared based on desired messenger RNA selected from various messenger RNA's extracted, for example, from the human placenta by a known method, by using a probe prepared based on the DNA sequence of FIG. 7 provided by the present invention. Alternatively, a part or all of this DNA can be chemically synthesized according to the disclosure of the present invention.

5. Expression Vector

As the replicable expression vector capable of expressing the DNA sequence coding human gp130 provided according to the present invention, any vector having a replicating origin, control sequences and a sequence coding for gp130, and capable of transforming a selected host can be appropriately used without limitation. For example, plasmids such as pBR322 and pBR327 can be used when E. coli is used as the host, and when cultured cells of a mammal or the like is used as the host, a vector having a DNA replicating origin derived from SV40 virus, can be used.

Of the control sequences for expressing the coding sequence, promoter system is important, and an appropriate promoter system should be elected according to the relationship to the selected host. When E. coli is used as the host, lactose promoter system, a tryptophan promoter system and hybrid promoter systems thereof are preferably selected. When cultured cells derived from a mammal are used as the host, an SV40 promoter system, adenovirus promoter system, and cytomegalovirus promoter system are preferably selected.

6. Host

Microorganisms or cultured cells customarily used for producing proteins by genetic engineering can be used as the host without limitation. As the microorganism, there can be mentioned E. coli such as K-12 or W-3110, Bacillus subtilis and yeast, and as the cultured cells, there can be mentioned COS cells (monkey renal fibroblast), CHO cells (Chinese hamster oocyte), and myeloma cells.

The host explained in (4) above, which has been transformed by the vector explained in (5) above, is cultured to express the DNA sequence coding for human gp130 in the vector DNA, whereby human gp130 is produced. This is realized by the activation of the promoter system in the control sequences linked to the DNA sequence coding for human gp130.

A polyclonal antibody or monoclonal antibody to the protein of the present invention can be prepared according to customary procedures by using the protein of the present invention prepared according to various processes as described above, or the cell producing this protein as an immunogen. As the cell source and animal to be used in this preparation process, there can be mentioned organisms such as human, mouse, rabbit, goat, and sheep.

The cell membrane-derived protein participating in the transmission of IL-6 signal, provided according to the present invention, can be used as a reagent for clarifying the signal transmission mechanism of IL-6 and developing valuable substances such as therapentic agents for controlling the function of IL-6. For example, by using, as a detection criterion, the property of the present protein which transmits IL-6 signal while being specifically bonded to the IL-6 receptor bonded to IL-6, substances controlling the function of IL-6 can be screened. As the substances to be screened, there can be mentioned natural substances, synthetic chemicals, IL-6 and an IL-6 receptor produced by a genetic engineering, derivatives thereof, and antibodies to IL-6, the IL-6 receptor, and antibodies to these proteins.

Furthermore, by bonding the soluble IL-6 receptor which has been bonded to IL-6 to the present protein, the function of IL-6 can be enhanced, and the function of IL-6 can be exerted even on a cell having no IL-6 receptor in the cell surface layer. On the other hand, if the bonding of the above-mentioned protein to the IL-6 receptor which has been bonded to IL-6 is inhibited by an antibody to IL-6, IL-6 receptor or the above-mentioned protein, the biological activity of IL-6 will be inhibited. Accordingly, it is considered that the protein of the present invention will be usable as an active ingredient of a medicine.

Furthermore, by the DNA sequence coding for human gp130 according to the present invention, and the means and process for producing this protein by genetic engineering, this protein, which is produced only in a very small amount in the natural state, can be produced in a large quantity.

The present invention will now be described in detail with reference to the following examples, that by no means limit the scope of the invention. Note, the protein of the present invention is sometimes called "gp130" in the examples for convenience.

EXAMPLE 1

Bonding of Protein (gp130) on Human Cell Membrane to Human IL-6 Receptor in Presence of Human IL-6

Human myeloma cells U266 (cells producing the IL-6 receptor and gp130 protein) ($2 \times 10^7$ cells) were internally labelled with 1 mCi of $^{35}$S-methionine and divided into two parts. One part was incubated in 0.5 ml of PRMI1640 at 37° C. for 30 minutes in the presence of IL-6 (1 μg/ml), and the other part was similarly incubated in the absence of IL-6. Then, the U266 cells were lysed with 1 ml of a 10 mM triethanolamine buffer solution (having a pH value of 7.4) containing 1% of digitonine (supplied by Wako Junyaku), 0.15M NaCl, and 1 mM pAPMSF (supplied by Wako Junyaku). Separately, the IL-6 receptor antibody MT18 (Referential Example 1) was bonded to Sepharose 4B activated by cyanogen bromide, and the bonded antibody then mixed with the supernatant of the above-mentioned cell lysate, whereby the solubilized IL-6 receptor was bonded to the MT18 antibody on the resin.

The non-specifically bonded substances were washed away by the above-mentioned solution containing 1% of digitonine. Then, under reducing or non-reducing conditions, the polyacrylamide gel electrophoresis in sodium dodecyl sulfate (SDS/PAGE) and the autoradiography were carried out. The results are shown in FIG. 1. In FIG. 1, the band of 80 kDa shows the $^{35}$S-methionine-labelled IL-6 receptor derived from the U266 cell, and the band of 130 kDa shows the gp130 protein of the present invention. From the results shown in FIG. 1, it is seen that the IL-6 receptor bonded to IL-6 is bonded to the human protein (gp130) having a monomer molecular weight of 130 kDa within 30 minutes at 37° C.

EXAMPLE 2

Bonding of Human IL-6 receptor to Protein (gp130) on Mouse Cell Membrane in Presence of Human IL-6

A plasmid prepared by inserting a human IL-6 receptor cDNA into the site of BamHI in the plasmid pZip-NeoSV(X)I (see Cepko et al, Cell, 37, page 1053, 1984) was introduced into a mouse B cell strain M12 not expressing the IL-6 receptor on the cell surface, by the electropolation method, and the transformed cell was screened based on the resistance to an antibiotic substance G418 (supplied by Sigma). The thus-established mouse B cell M12-derived clone expressing the human IL-6 receptor on the cell surface was named "M12IL6R".

Figure 2:
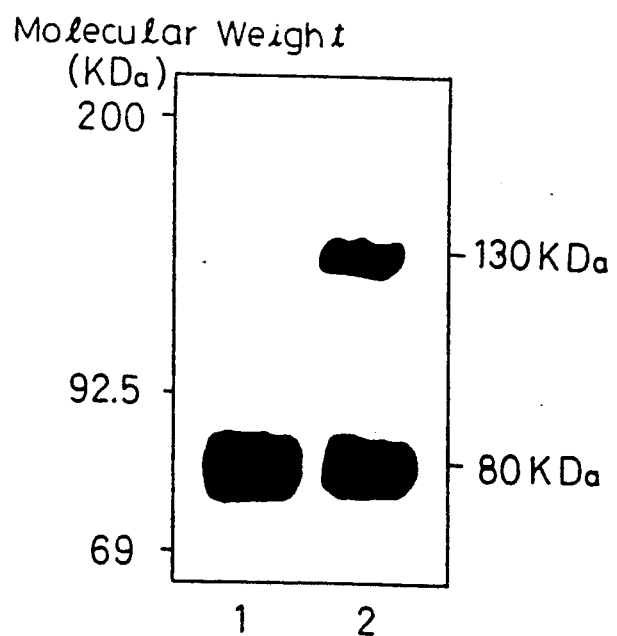
FIG. 2 shows autoradiographic patterns obtained when M12IL6R cells surface-labelled with $^{125}$I are lysed after treatment with IL-6 (lane 2) or without treatment with IL-6 (lane 1), and is then treated in the same manner as in FIG. 1.

Then, $10^7$ of M121L6R cells were washed with PBS and suspended in 0.1 ml of 50 mM Tris (having a pH value of 7.4) and 0.15M NaCl. Next, 1 mCi of Na $^{125}$I and two Iodobeads (supplied by Pierce) were reacted at room temperature for 5 minutes in 0.1 ml of the above-mentioned buffer solution, the reaction liquid was mixed with the above-mentioned cell suspension, and incubation was carried out at room temperature for 30 minutes. Then 1 μg/ml of IL-6 was added to the thus-labelled cells, or was not added, and the reaction was carried out at 37° C. for 30 minutes, the cell was lysed according to the method described in Example 1, an immunoprecipitation by MT18 was carried out, and the SDS/PAGE and autoradiography were then carried out. The results are shown in FIG. 2. In FIG. 2, the band of 80 kDa shows the IL-6 receptor produced by the IL-6 receptor cDNA introduced into an M12 cell, and the band of 130 kDa shows a gp130 protein inherently produced by the M12 cell. From the results shown in FIG. 2, it is seen that the human IL-6 receptor on M12IL6R bonded to the human IL-6 is bonded to the mouse protein (gp130) derived from M12IL6R, at 37° C. within 30 minutes.

EXAMPLE 3

Bonding of Soluble IL-6 Receptor to gp130 in Presence of IL-6

Figure 3:
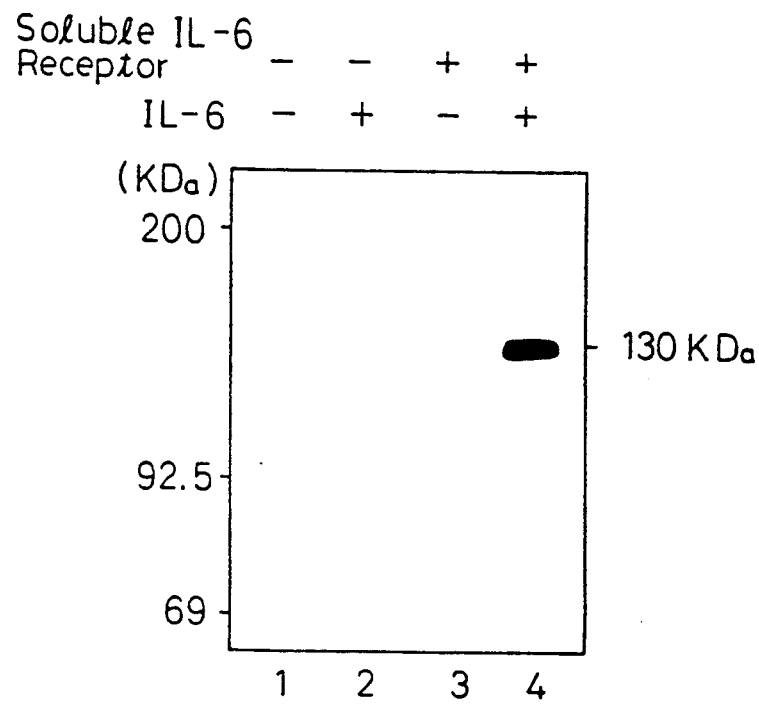
FIG. 3 shows autoradiographic patterns obtained when M12 cells are incubated in the presence (lanes 2 and 4) or absence (lanes 1 and 3) of IL-6 and in the presence of a culture supernatant of COS7 cells containing soluble IL-6 receptor (lanes 3 and 4) or not containing soluble IL-6 receptor (lanes 1 and 2) and lysed, and is then treated in the same manner as in FIG. 1.

According to the method described in Example 2, $2 \times 10^7$ of M12 cells (cells not producing IL-6 receptor) were labelled, $5 \times 10^6$ of the labelled cells were added to 1 ml of a culture supernatant of COS7 cells containing or not containing the soluble IL-6 receptor in the presence or presence of IL-6 (1 μg/ml), and the reaction was carried out at 37° C. for 30 minutes. Then the cells were lysed with digitonine according to the method described in Example 1, immunoprecipitation was carried out by MT18 antibody, and the SDS/PAGE and autoradiography were then carried out. The results are shown in FIG. 3. In FIG. 3, the band of 130 kDa shows the gp130 protein produced by M12 cells. Note, in this example, since the soluble IL-6 receptor was not labelled, this receptor was not shown by the autoradiography. From the results shown in FIG. 3, it is seen that the complex of IL-6 and the soluble IL-6 receptor is bonded to the protein (gp130) on the cell membrane, and the soluble IL-6 receptor alone is not bonded to gp130.

EXAMPLE 4

Enhancement of Function of IL-6 by Soluble IL-6 Receptor in Presence of IL-6

Figure 4:
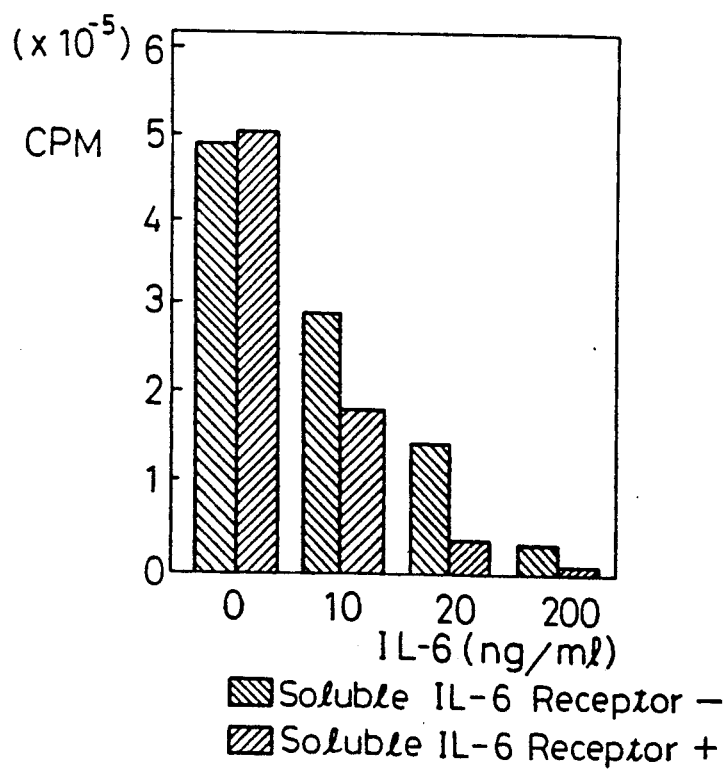
FIG. 4 shows incorporation of $^3$H-labelled thymidine by MI cells in the presence of IL-6 at various concentrations, and in the presence or absence of a soluble IL-6 receptor.

M1 cells ($1 \times 10^5$ cells/ml) were cultured at 0.2 ml/well in a culture medium containing IL-6 at various concentration as well as COS7 cell supernatant or soluble IL-6 receptor-containing COS7 cell supernatant in an amount of 25%. Within 60 to 70 hours from the start of the culturing, $^3$H-labelled thymidine was added, and by measuring the radioactivity incorporated into the cells, the proliferation of the cells was examined. FIG. 4 shows that the effect of inhibiting the proliferation of M1 cells, possessed by IL-6, is enhanced by the soluble IL-6 receptor. Namely, the function of IL-6 is enhanced by the bonding of the IL-6-bonded soluble IL-6 receptor to gp130 of M1 cell.

EXAMPLE 5

Isolation of Human gp130 cDNA

A series of gene recombination operations (extraction of m-RNA, cleavage of DNA by restriction enzyme, and the like) were carried according to the process of Maniatis et al (see Molecular Cloning, Cold Spring Harbor Laboratory, 1982) and the process of Harwin et al (see DNA Cloning, A Practical Approach, vol. 1, page 49, IRL, Oxford, 1985). Screening by the antibody of λgtll cDNA library was carried out according to the conventional method.

Figure 5:
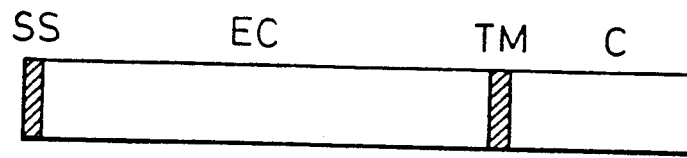
FIG. 5 shows a restriction enzyme map of λA and λB and a schematic structure of a corresponding human gp130 protein, in which E represents the EcoRI site, SS represents the signal sequence, EC represents the extracellular region, TM represents the membrane penetration region, and C represents the intracellular region.

First, a messenger (m) RNA was extracted from human myeloma cell U266 (see Cell, volume 58, page 573, 1989), and a cDNA library was prepared by using λgtII (supplied by Clontech). Then, using mouse-derived monoclonal antibodies AM64 and AM277 (see Japanese Patent Application No. 2-15090) to gp130, about 500,000 clones were screened, and finally, two coulones ($\lambda_A$ and $\lambda_B$) were obtained. The insert cDNA of each of $\lambda_A$ and $\lambda_B$ was analyzed, and the results are shown in FIG. 5. As shown in FIG. 5, the insert cDNAs did not contain the full length human gp130-coding region.

Figure 6:
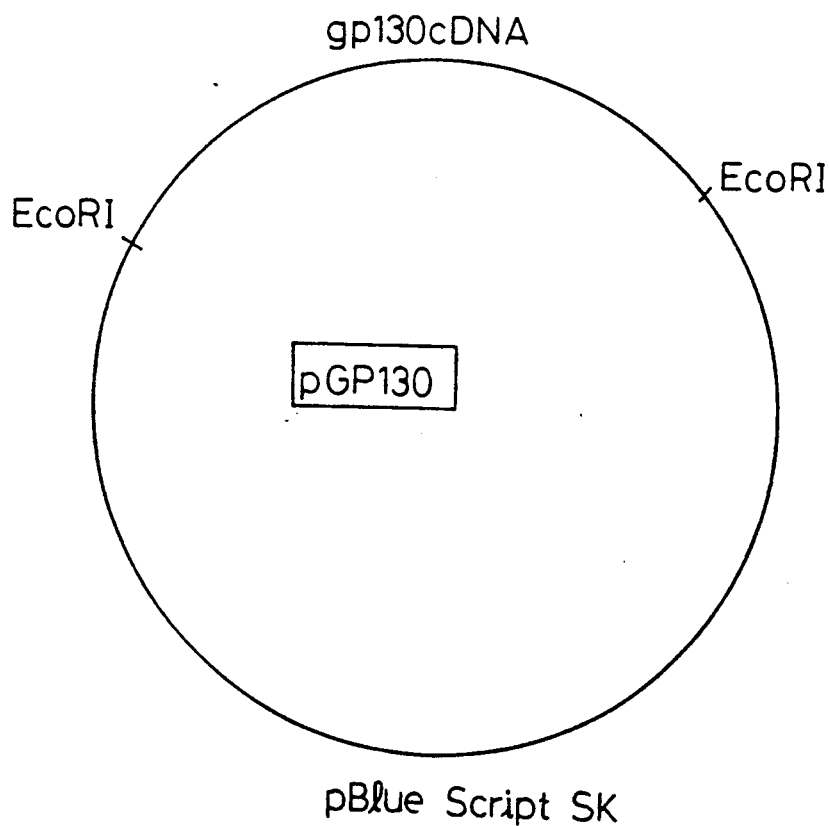
FIG. 6 shows the structure of pGP130.

Accordingly, an EcoRI fragment of $\lambda_A$ and the EcoRI fragment of $\lambda_B$ were inserted, while connecting them in the orientation of reading of cDNA, to the EcoRI site of a vector pBlueScript SK (supplied by Stratagene) to prepare a plasmid pGP130 having an insert DNA containing the complete human gp130-coding region. The structure of pGP130 is shown in FIG. 6, and the sequence of the insert DVA of pGP130, i.e., the sequence of human gp130 cDNA determined from insert cDNA sequences of $\lambda_A$ and $\lambda_B$, and the presumed amino acid sequence, are shown in FIG. 7.

Note, E. coli HB101/pGP130 containing this plasmid pGP130 was internationally deposited as deposition No. FERM BP-2912 under the Budapest Treaty on May 15, 1990 with the Fermentation Research Institute, Agency of Industrial Science and Technology, located at 1-3, Higashi 1-Chome, Tsujuka-shi, Ibaragi-ken, Japan.

EXAMPLE 6

Expression of Human gp130 mRNA in Various Cells

To examine the expression of human gp130 in various cells, Northern blot analysis was carried out. The culturing of cells, extraction of mRNA from the cells, electrophoresis, blotting, probe labelling, hybridization, filter washing, and autoradiography were carried out according to standard methods.

mRNA was extracted from human myeloma cells U266, human B cells CESS, human Burkitt's lymphoma Jijoye, human T cells Jurkat, and NK cells YT, and 1 μg of each mRNA then denatured by the formamide method and subjected to electrophoresis with 0.8% agarose gel, and to Northern blotting on a nylon filter membrane. Then an insert cDNA of $\lambda_A$ obtained by the method described in Example 5 was extracted, and using this extracted insert cDNA, hybridization was carried out at 42° C. for 24 hours. The product was then washed and autoradiography was carried out.

Figure 8:
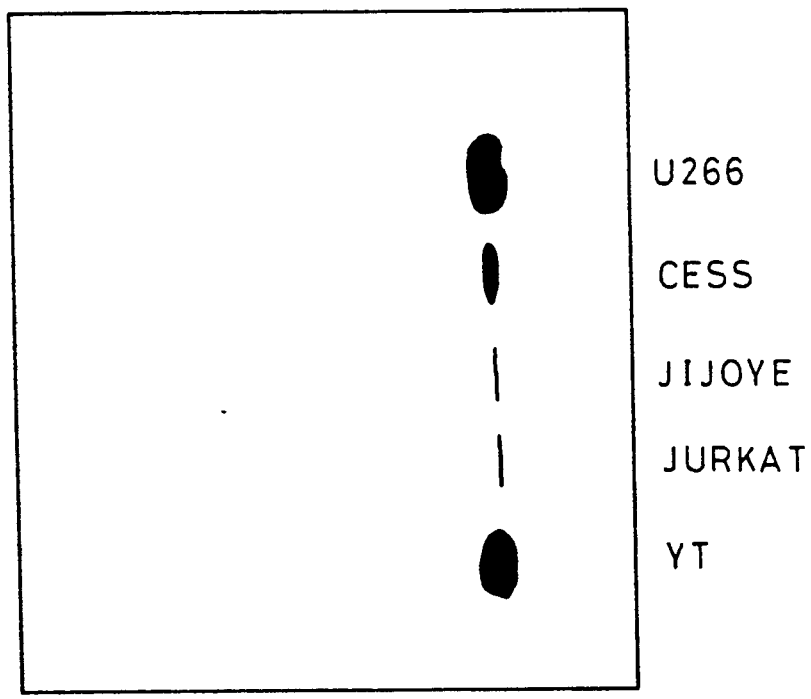

The results are shown in FIG. 8, and it is seen that the manifestation of gp130 mRNA is strong in U266 and YT, medium in CESS, and weak in Jijoye and Jurkat. This has a relation to the reactivity of the IL-6 of each cell.

REFERENTIAL EXAMPLE 1

Preparation of Monoclonal Antibody to Human IL-6 Receptor

To prepare a mouse monoclonal antibody to human IL-6 receptor, a mouse T cells having human IL-6 receptors expressed on the cell membrane surface was prepared as an antigen, according to the following method. More specifically, pBSF2R.236 and pSV2neo disclosed in Japanese Patent Application No. 1-9744 were introduced in mouse T-cells CTLL-2 (ATCC, TIB214) according to a customary procedure, and screening was carried out according to the conventional method using G-418. Finally, the strain in which about 30,000 IL-6 receptors per cell were expressed was established, and this strain was named "CTBC2".

The immunization was carried out in the following manner. The CTBC2 cells were cultured according to a conventional method using PRMI1640, and the cultured CTBC cells were washed four times with a PBS buffer and used intraperitoneally to immunize C57BL6 mouse in an amount of $1 \times 10^7$ cells per mouse once a week, six times as a whole.

The spleen cells of the immunized mouse were fused to the myeloma cells P3U1 as the parent cell line, according to a conventional method using polyethylene glycol.

Screening was carried out in the following manner. Namely, pBRF2R.236 and PSV2neo were introduced into the IL-6 receptor-negative human T cell strain JURKAT (ATCC, CRL8163) according to a conventional method, and by the screening, a strain expressing about 100,000 IL-6 receptors per cell was established, and this stain was named "NJBC8". One clone of the hybridoma producing an antibody recognizing NJBC8 lysed by NP40 but not recognizing JURKAT lysed by NP40 was isolated and named "MT18". The monoclonal antibody produced by this hybridoma was named "MT18 antibody".

The above-mentioned hybridoma MT18 was deposited at the Fermentation Research Institute (FRI) Agency of Industrial Science and Technology 1-3 Yatabe-cho Higashi 1-chome Ibaraki Japan as FERM P-10840 on Jul. 12, 1989, and transferred to an international deposition under the Budapest Treaty as FERM BP-2999 on Jul. 10, 1990.

I claim:

1. Purified DNA coding for human gp130 protein, wherein said protein
   (1) has a monomeric molecular weight of approximately 130 kDa in SDS-polyacrylamide electrophoresis;
   (2) is associated with the cell membrane; and
   (3) is capable of forming a complex with IL-6 and an IL-6receptor which is required in order for IL-6 to induce cellular proliferation and differentiation.

2. DNA as set forth in claim 1, which codes for a human gp130 protein having an amino acid sequence of from Met at the 1st position to Bln at the 918th position in FIG. 7.

3. DNA as set forth in claim 1, which has a nucleotide sequence as set forth in FIG. 7 from A at the 273rd position to G at the 3026th position.

4. An expression vector containing DNA as set forth in claim 1 and capable of expressing said DNA in a host cell.

5. A process for the production of human gp130 protein, which comprises culturing host cells transformed by an expression vector as set forth in claim 4.

* * * * *